(12) United States Patent
Prueter

(10) Patent No.: US 6,631,888 B1
(45) Date of Patent: Oct. 14, 2003

(54) BATTERY OPERATED FRAGRANCE DISPENSER

(75) Inventor: David M. Prueter, Olathe, KS (US)

(73) Assignee: Saint-Gobain Calmar Inc., City of Industry, CA (US)

( * ) Notice: Subject to any disclaimer, the term of this patent is extended or adjusted under 35 U.S.C. 154(b) by 0 days.

(21) Appl. No.: 10/141,949

(22) Filed: May 10, 2002

(51) Int. Cl.⁷ .................................................. B01F 3/04
(52) U.S. Cl. ................ 261/30; 261/104; 261/DIG. 88; 422/124; 239/57
(58) Field of Search ............................ 261/30, 95, 104, 261/DIG. 88; 422/124; 239/55, 56, 57, 60

(56) References Cited

U.S. PATENT DOCUMENTS

| | | | |
|---|---|---|---|
| 3,990,848 A | 11/1976 | Corris | 21/126 |
| 4,111,655 A | 9/1978 | Quincey | 422/124 |
| 4,840,770 A | 6/1989 | Walz et al. | 422/49 |
| 4,865,816 A | 9/1989 | Walz et al. | 422/123 |
| 5,342,584 A * | 8/1994 | Fritz et al. | 422/124 |
| 5,370,829 A | 12/1994 | Kunze | 261/24 |

FOREIGN PATENT DOCUMENTS

US  2002/0005437 A1  1/2002  ................. 239/13

* cited by examiner

*Primary Examiner*—Robert Hopkins
(74) *Attorney, Agent, or Firm*—Dykema Gossett PLLC

(57) ABSTRACT

A fragrance dispenser includes a container for holding and exposing a fragrance material, and a housing defined by at least one elongated shell and a cap including an elongated slider. Each elongated shell is slideably engageable with the elongated slider. The housing includes an air discharge opening on the cap, and a power source mounted therein for providing power to a motor, which is operably connected to drive a fan. The fan is operable to increase flow of air over the fragrance material, to dispense fragrance from within the housing, through the air discharge opening, to an exterior of the housing. When the at least one elongated shell is engaged to the cap, the power source supplies power to the motor to drive the fan, and when the at least one elongated shell is disengaged from the cap, power from the power source to the motor is discontinued.

37 Claims, 2 Drawing Sheets

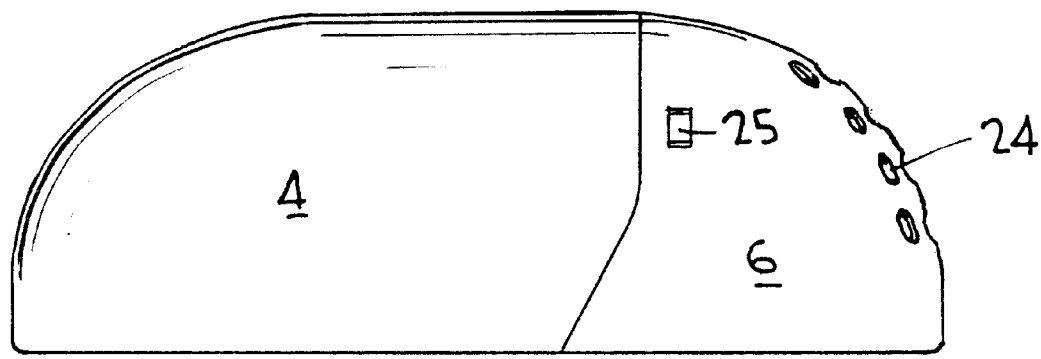
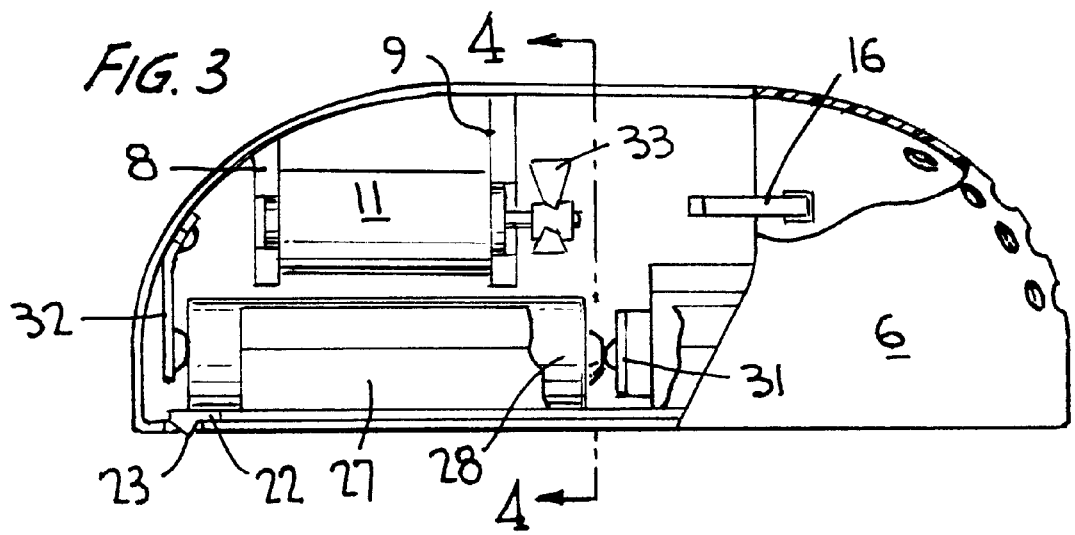
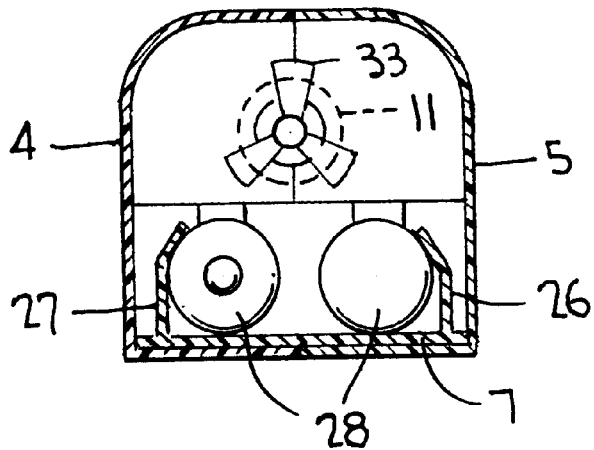

BATTERY OPERATED FRAGRANCE DISPENSER

BACKGROUND OF INVENTION a. Field of Invention

The invention relates generally to an apparatus for producing fragrance, and, more particularly to a fragrance dispensing device that automatically emits fragrance by providing a self-contained unit which houses a battery-powered fan for increasing flow of air over a fragrance material, so as to dispense fragrance from within the unit and out through an air discharge opening.

b. Description of Related Art

A need exists for a device that can be easily assembled and disassembled, a device that includes fewer parts for ease of manufacturing, and a device that is simple to operate.

While conventional fragrance dispensing devices provide a means of automatically dispensing fragrance, such devices are often difficult to operate because of their design complexity. Such devices also do not adequately dispense fragrance over a large area. Moreover, such devices include multiple components that can be difficult to manufacture and assemble, thus making the device expensive and unreliable.

In the art, there currently exist devices for automatically dispensing fragrance or insect repellant, as disclosed for example in the Published U.S. patent application to Ketcha et al. (Pub. No. US 2002/0005437). The Ketcha device is a personal protection device for repelling insects. The device includes a cartridge, which includes a composition comprising insect repellant. The device further includes an atomizer for actively dispersing the composition, causing the composition to be removed from the cartridge and to be dispersed in an area around a subject.

Other U.S. Patents related to battery powered fragrance dispensers include U.S. Pat. Nos. 5,370,829, 4,865,816, 4,840,770, 4,111,655 and 3,990,848. The fragrance dispensers disclosed in these Patents include basic components such as a motor for driving a fan, an electrical or mechanical power source for supplying power to the motor, and a fragrance source.

These conventional fragrance dispensers however have several disadvantages. Some of the key drawbacks generally include an excessive number of components, which can make the device difficult and expensive to manufacture. Additionally, because of the excessive number of components, the odds of essential components being damaged or destroyed during use is increased, thus rendering the device inoperable. Because of design flaws, conventional fragrance dispensers can also be dangerous to operate as they may require the handling of corrosive components such as batteries, which may be corroded by, for example, interaction with the fragrance material or other such materials. Moreover, for the average consumer, conventional devices can be difficult to operate as they may require sophisticated assembly, disassembly and operation procedures.

SUMMARY OF INVENTION

The invention solves the problems and overcomes the drawbacks and disadvantages of the prior art by providing a fragrance dispenser which has relatively few components for ease of assembly and disassembly, is simple and relatively inexpensive to manufacture, and is safer to handle and operate.

In particular, the invention accomplishes this by providing a fragrance dispenser, which includes a container for holding and exposing a fragrance material. The fragrance dispenser further includes a housing defined by at least one elongated shell and a cap including an elongated slider. The or each elongated shell is slideably engageable with the elongated slider on the cap. The container is disposed within the housing. The housing also includes at least one air discharge opening, which may be in the form of a perforated wall of either the elongated shell or the cap. The fragrance dispenser further includes a power source mounted in the housing and supported by the elongated slider. A fan is driven by a motor powered by a power source, all of which are mounted in the housing. The fan is operable to increase flow of air over the fragrance material and to dispense fragrance from within the housing through the air discharge opening to an exterior of the housing. When the elongated shell is engaged with the cap, the power source supplies power to the motor to drive the fan, and when the elongated shell is disengaged from the cap, power from the power source to the motor is discontinued.

In the fragrance dispenser, the fragrance material may be a solid, a liquid or a gel. The elongated shell includes a first elongated shell and a second elongated shell, which are slidably engageable with the elongated slider on the cap. The first and second elongated shells are mirror images of each other, and each may include a cradle support for the motor. Each of the first and second elongated shells may also include a resilient engagement member for permitting detachable engagement with the cap. The engagement member may include a resilient snap-fit member including a tongue for snapping into a slot in the cap. Each of the first and second elongated shells may also include a cutout for permitting detachable engagement with a lock member on the cap. The cap may further include an elongated support structure mounted to the elongated slider for supporting the power source. The power source may include at least one battery, and first and second battery contacts for transmitting power to the motor. The first battery contact is disposed between the batteries and the container and supported by the elongated slider, and the second battery contact may be fixedly mounted to the elongated shell. The second battery contact is connected to the battery when the elongated shell is engaged with the cap, and is disconnected from the battery when the elongated shell is disengaged from the cap. Additionally, in the fragrance dispenser, the container and the housing may be of a plastic, a ceramic or a metal.

In yet another aspect of the invention, the invention solves the problems and overcomes the drawbacks and disadvantages of the prior art by providing a fragrance dispenser including a container for holding and exposing a fragrance material. The fragrance dispenser further includes a housing defined by at least two connectable members. Each of the two connectable members is capable of detachable engagement with another of the two connectable members. The housing also includes at least one air discharge opening on at least one of the two connectable members. The fragrance dispenser further includes a power source mounted in the housing. An air-moving source is mounted in the housing and driven by a motor also mounted in the housing. The motor is powered by the power source. The air-moving source is operable to increase flow of air around the fragrance material, to dispense fragrance from within the housing, through the at least one air discharge opening, to an exterior of the housing. When one of the two connectable members is in an engaged configuration with another of the two connectable members, the power source supplies power to the motor to drive the air-moving source, and when one of the two connectable members is in a disengaged configuration from another of the two connectable members, power from the power source to the motor is discontinued.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIG. 2 is a side view of the fragrance dispenser of the assembled FIG. 1 components;

FIG. 3 is a partial sectional of the fragrance dispenser depicting the layout of some of the inner components; and FIG. 4 is a cross-sectional view of the front portion of the fragrance dispenser taken along line 4—4 in FIG. 3.

DETAILED DESCRIPTION OF THE PREFERRED EMBODIMENT

Figure 1:
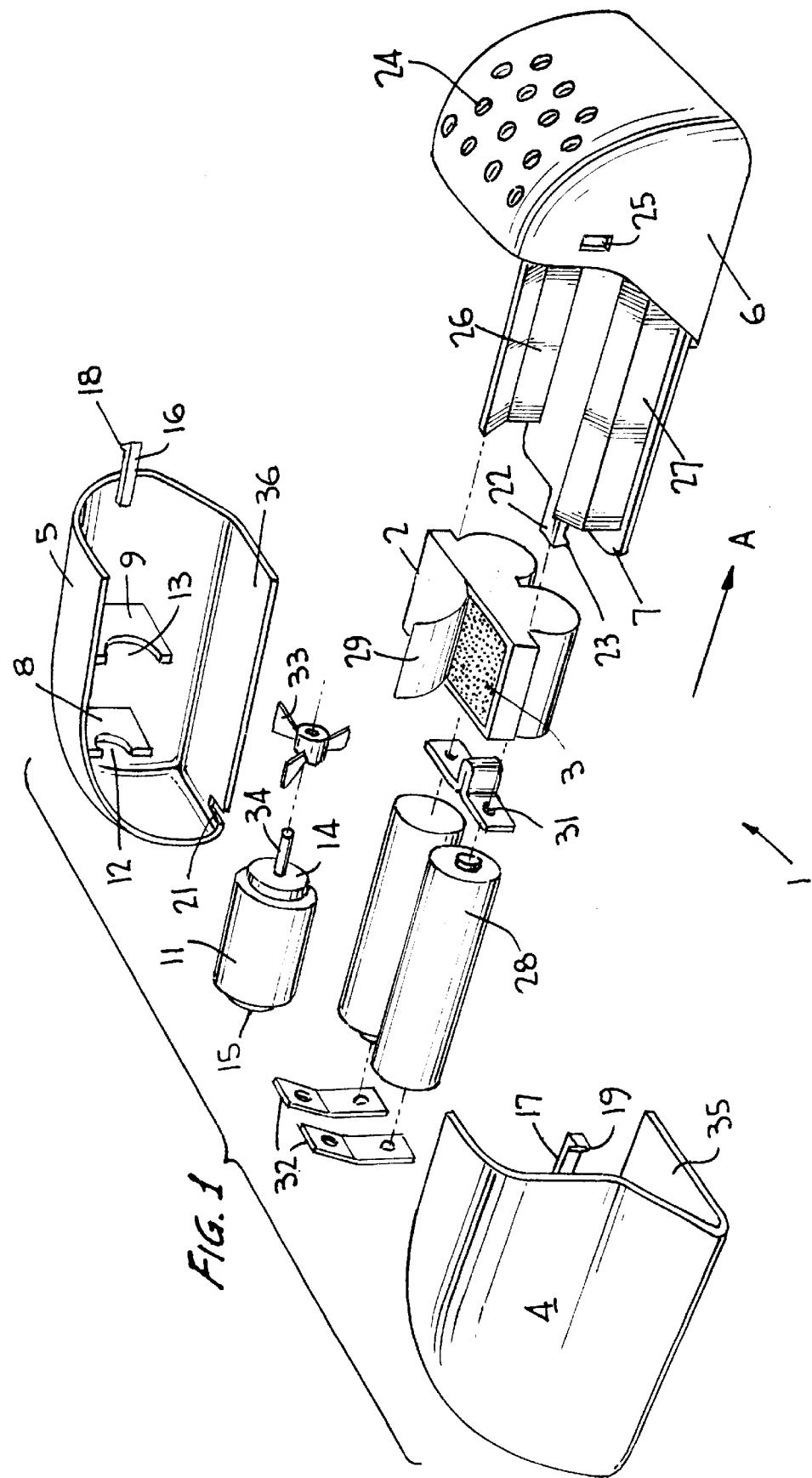
FIG. 1 is an exploded view of the preferred embodiment of the fragrance dispenser according to the present invention showing the device components in a disassembled configuration.

As shown in FIG. 1, the fragrance dispenser generally designated 1 has disposed therein a container 2 for holding and exposing fragrance material 3. Fragrance dispenser 1 includes a housing defined by two elongated shells 4 and 5, and a cap 6 (hereinafter, the general term housing will be used to refer to the structure formed by the two elongated shells 4 and 5, and cap 6). Cap 6 includes an elongated slider 7 for permitting relative sliding between elongated shells 4 and 5 and cap 6.

The housing components will now be described in greater detail.

In the preferred embodiment, elongated shells 4 and 5 each include supports 8 and 9 (shown only for elongated shell 5) for a motor 11. Supports 8 and 9 include complementary arc-shaped (or cradle-shaped) cutouts 12 and 13, respectively, for supporting motor 11 at ends 14 and 15, respectively. Each elongated shell 4 and 5 further includes resilient snap-fit members 16 and 17, respectively, each having tongues 18 and 19, respectively, at the ends thereof. Each elongated shell 4 and 5 also includes an identical cutout 21 (only shown for elongated shell 5) for providing locking engagement with lock member 22, having a nib 23, on elongated slider 7.

Elongated shells 4 and 5 are mirror images of each other and may be formed by injection molding. Alternatively, elongated shells 4 and 5 may be cast, or manufactured by any of the equivalent manufacturing methods known in the art. Elongated shells 4 and 5 may be of a plastic, ceramic, metallic or equivalent material. Additionally, as shown in FIG. 1, each elongated shell 4 and 5 has a contoured outer surface. Alternatively, it would be apparent to a skilled artisan that elongated shells 4 and 5 may be formed of various ergonomic shapes as deemed necessary.

Cap 6 includes air discharge opening 24, which is shown as a plurality of perforations in FIG. 1. Cap 6 also includes two slots 25 (only one shown in FIG. 1) for retention of tongues 18 and 19 on resilient snap-fit members 16 and 17, respectively. Cap 6 yet further includes two mirror-image elongated supports 26 and 27 for supporting power source 28 (discussed in greater detail below).

Cap 6 may be manufactured by injection molding, or alternatively, may be manufactured by casting or by any of the equivalent manufacturing methods known in the art. Cap 6 may be made from a plastic, ceramic, metallic or equivalent material. Cap 6 may include a contoured outer surface (as shown in FIG. 1), or alternatively, formed of various ergonomic shapes as apparent to a skilled artisan. Air discharge opening 24 may be formed during the molding process or may be stamped or punched after molding. The perforations defining air discharge opening 24 may be randomly or symmetrically disposed, and may include various cross-sections such as circular, elliptical and/or rectangular. Alternatively, air discharge opening 24 may be in the form of slits or other equivalent cutouts, or is otherwise porous. Air discharge opening 24 may also be provided on elongated shells 4 and 5 and/or cap 6.

Next, the components located inside the housing will be described.

As discussed above, container 2, which is disposed within cap 6, holds fragrance material 3. As shown in the preferred embodiment in FIG. 1, container 2 includes a peel-off cover 29, which would be removed to expose fragrance material 3.

Container 2 may be manufactured by injection molding, or alternatively, may be cast or manufactured by any of the equivalent manufacturing methods know in the art. Container 2 may be made from a plastic, ceramic, metallic or equivalent material, as would be apparent to a skilled artisan. Fragrance material 3 may be any combination of a solid, a liquid or a gel substance. Moreover, fragrance material 3 may be any of the variety of well known materials in the art that may be injected or formed inside container 2 during or after the manufacture thereof.

Fragrance dispenser 1 further includes power source 28 (as discussed above) mounted in the housing and supported by elongated slider 7 (see FIG. 4). In the preferred embodiment, power source 28 includes two batteries. Alternatively, power source 28 may include a single battery, or multiple batteries, capable of driving motor 11. Power source 28 supplies power to motor 11 via first and second contacts 31 and 32. As shown in FIGS. 1 and 3, contact 31 is disposed between container 2 and power source 28, and contacts 32 (one for each elongated shell 4 and 5) are fixedly mounted to each elongated shell 4 and 5. Contacts 31 and 32 may be cast in their final shape (i.e. the bent configuration shown in FIG. 1) or bent from a piece of electrically conductive material. Additionally, contacts 32 may be removably mounted to each of the elongated shells 4 and 5.

Fragrance dispenser 1 yet further includes a fan 33 mounted to shaft 34 of motor 11. Fan 33 operates to increase flow of air over and around fragrance material 3, to dispense fragrance from within the housing, through air discharge opening 24, and to an exterior of the housing. Thus fan 33 causes fragrance emitted from fragrance material 3 to be expelled through air discharge opening 24.

The assembly, disassembly and operation of fragrance dispenser 1 will now be described in detail.

In order to assemble fragrance dispenser 1, peel-off cover 29 on container 2 may first be removed and container 2 may be inserted into cap 6. Next, power source 28 may be inserted between elongated supports 26 and 27 on elongated slider 7 (see FIGS. 3 and 4). Thereafter, the assembly defined by elongated shells 4 and 5, which generally includes motor 11, contacts 32, and fan 33 may be slid relative to elongated slider 7 on cap 6. Specifically, surfaces 35 and 36 of elongated shells 4 and 5, respectively, may be slid in the direction of arrow A (see FIG. 1), under elongated slider 7. This sliding motion would continue until tongues 18 and 19 on resilient snap-fit members 16 and 17, respectively, fully engage slots 25 on cap 6, and nib 23 on lock member 22 fully engages cutout 21.

It should be noted that the assembly procedure discussed above is just one of many methods of assembling fragrance dispenser 1, as would be apparent to a skilled artisan.

In order to disassemble fragrance dispenser 1, a pointed edge (i.e. a flat screwdriver) may be inserted into cutout 21 and slots 25, in order to release nib 23 and tongues 18 and 19, respectively. Thereafter, the assembly defined by elongated shells 4 and 5 may be removed from the assembly defined by cap 6 by means of a sliding motion opposite the direction of arrow A, relative to elongated slider 7.

Likewise, it should be noted that the disassembly procedure discussed above is just one of many methods of disassembling fragrance dispenser 1, as would be apparent to a skilled artisan.

In order to operate (activate) fragrance dispenser 1, the circuit defined by contacts 31 and 32, power source 28 and motor 11 must be completed. This can be achieved by engaging the assembly defined by elongated shells 4 and 5 to the assembly defined by cap 6. Therefore, one method of activating fragrance dispenser 1 would be to follow the assembly procedures discussed above. Likewise, one method of de-activating fragrance dispenser 1 would be to follow the disassembly procedures discussed above. Moreover, it should be apparent from the above discussion that activation of fragrance dispenser 1 requires elongated shells 4 and 5 to be fully engaged to cap 6, and de-activation of fragrance dispenser 1 only requires elongated shells 4 and 5 to be partially disengaged from cap 6.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A fragrance dispenser, comprising:
    a container for holding and exposing a fragrance material;
    a housing defined by at least one elongated shell and a cap including an elongated slider, each said at least one elongated shell being slideably engageable with said elongated slider on said cap, said container disposed within said housing, said housing further comprising at least one air discharge opening;
    a power source mounted in said housing and supported by said elongated slider;
    a fan mounted in said housing; and
    a motor mounted in said housing and powered by said power source, said motor being operably connected to drive said fan, said fan being operable to increase flow of air over said fragrance material, to dispense fragrance from within said housing, through said at least one air discharge opening, to an exterior of said housing,
    wherein when said at least one elongated shell is engaged to said cap, said power source supplies power to said motor to drive said fan, and when said at least one elongated shell is disengaged from said cap, power from said power source to said motor is discontinued.

2. The fragrance dispenser according to claim 1, wherein said fragrance material is at least one of a solid, a liquid or a gel.

3. The fragrance dispenser according to claim 1, wherein said container is disposed within said cap.

4. The fragrance dispenser according to claim 1, wherein said at least one elongated shell comprises a first elongated shell and a second elongated shell, each said first and said second elongated shell being slidably engageable with said elongated slider on said cap.

5. The fragrance dispenser according to claim 4, wherein each said first elongated shell and said second elongated shell comprises a support for said motor.

6. The fragrance dispenser according to claim 5, wherein said support comprises at least one cradle member.

7. The fragrance dispenser according to claim 4, wherein each said first elongated shell and said second elongated shell comprises an engagement member for permitting detachable engagement with said cap.

8. The fragrance dispenser according to claim 7, wherein said engagement member comprises a resilient snap-fit member including a tongue for snapping into a slot in said cap.

9. The fragrance dispenser according to claim 4, wherein said first elongated shell is a mirror image of said second elongated shell.

10. The fragrance dispenser according to claim 4, wherein said cap and said first and second elongated shells comprise curved surfaces.

11. The fragrance dispenser according to claim 4, wherein each said first and second elongated shell comprises a cutout for permitting detachable engagement with a lock member on said cap.

12. The fragrance dispenser according to claim 1, wherein said cap further comprises an elongated support structure mounted to said elongated slider for supporting said power source.

13. The fragrance dispenser according to claim 1, wherein each said at least one air discharge opening comprises a plurality of perforations.

14. The fragrance dispenser according to claim 13, wherein said perforations are disposed on at least one of said at least one elongated shell or said cap.

15. The fragrance dispenser according to claim 1, wherein each said at least one air discharge opening comprises at least one of a plurality of slits or cutouts.

16. The fragrance dispenser according to claim 1, wherein said power source comprises at least one battery.

17. The fragrance dispenser according to claim 1, wherein said power source comprises at least one battery,
    said fragrance dispenser further comprising a first battery contact and a second battery contact, said first battery contact being disposed between said at least one battery and said container and supported by said elongated slider, and said second battery contact being fixedly mounted to said at least one elongated shell.

18. The fragrance dispenser according to claim 17, wherein said second battery contact is connected to said at least one battery when said at least one elongated shell is engaged to said cap, and is disconnected from said at least one battery when said at least one elongated shell is disengaged from said cap.

19. The fragrance dispenser according to claim 1, wherein said container and said housing are formed by at least one of a plastic, a ceramic or a metal.

20. A fragrance dispenser, comprising:

a container for holding and exposing a fragrance material;

a housing defined by at least two connectable members, each of said at least two connectable members being capable of detachable engagement with another of said at least two connectable members, at least one of said at least two connectable members comprising at least one air discharge opening;

a power source mounted in said housing;

an air-moving source mounted in said housing; and a motor mounted in said housing and driven by said power source, said motor being operably connected to drive said air-moving source, said air-moving source being operable to increase flow of air around said fragrance material, to dispense fragrance from within said housing, through said at least one air discharge opening, to an exterior of said housing, wherein when one of said at least two connectable members is in an engaged configuration with another of said at least two connectable members, said power source supplies power to said motor to drive said air-moving source, and when one of said at least two connectable members is in a disengaged configuration from another of said at least two connectable members, power from said power source to said motor is discontinued, and wherein at least one of said at least two connectable members comprises an elongated slider whereby another of said at least two connectable members may slide relative to said elongated slider.

21. The fragrance dispenser according to claim 20, wherein said fragrance material is at least one of a solid, a liquid or a gel.

22. The fragrance dispenser according to claim 20, wherein said container is disposed within said connectable member comprising said elongated slider.

23. The fragrance dispenser according to claim 20, wherein said at least two connectable members further comprise a first elongated shell and a second elongated shell, each said first and said second elongated shell being slidably engageable with said elongated slider.

24. The fragrance dispenser according to claim 23, wherein each said first elongated shell and said second elongated shell comprises a support for said motor.

25. The fragrance dispenser according to claim 24, wherein said support comprises at least one cradle member.

26. The fragrance dispenser according to claim 23, wherein each said first elongated shell and said second elongated shell comprises an engagement member for permitting detachable engagement with said connectable member comprising said elongated slider.

27. The fragrance dispenser according to claim 26, wherein said engagement member comprises a resilient snap-fit member including a tongue for snapping into a slot in said connectable member comprising said elongated slider.

28. The fragrance dispenser according to claim 23, wherein said first elongated shell is a mirror image of said second elongated shell.

29. The fragrance dispenser according to claim 23, wherein said connectable member comprising said elongated slider and said first and second elongated shells comprise curved surfaces.

30. The fragrance dispenser according to claim 23, wherein each said first and second elongated shell comprises a cutout for permitting detachable engagement with a lock member on said connectable member comprising said elongated slider.

31. The fragrance dispenser according to claim 20, wherein said connectable member comprising said elongated slider further comprises an elongated support structure mounted to said elongated slider for supporting said power source.

32. The fragrance dispenser according to claim 20, wherein each said at least one air discharge opening comprises a plurality of perforations.

33. The fragrance dispenser according to claims 32, wherein said perforations are disposed on at least one of said connectable members.

34. The fragrance dispenser according to claim 20, wherein each said at least one air discharge opening comprises at least one of a plurality of slits or cutouts.

35. The fragrance dispenser according to claim 20, wherein said power source comprises at least one battery.

36. The fragrance dispenser according to claim 20, wherein said power source comprises at least one battery, said fragrance dispenser further comprising a first battery contact and a second battery contact, said first battery contact being disposed between said at least one battery and said container, and supported by said elongated slider, and said second battery contact being fixedly mounted to another of said at least two connectable members.

37. The fragrance dispenser according to claim 36, wherein said second battery contact is connected to said at least one battery when one of said at least two connectable members is engaged to said connectable member comprising said elongated slider, and is disconnected from said at least one battery when said one of said at least two connectable members is disengaged from said connectable member comprising said elongated slider.

* * * * *